United States Patent
Salehi et al.

(10) Patent No.: US 9,693,869 B2
(45) Date of Patent: Jul. 4, 2017

(54) ORTHOPEDIC INSERT SYSTEMS AND METHODS

(71) Applicant: Smith & Nephew, Inc., Memphis, TN (US)

(72) Inventors: Abraham B. Salehi, Bartlett, TN (US); Brian W. McKinnon, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 144 days.

(21) Appl. No.: 14/366,516

(22) PCT Filed: Dec. 19, 2012

(86) PCT No.: PCT/US2012/070529
§ 371 (c)(1),
(2) Date: Jun. 18, 2014

(87) PCT Pub. No.: WO2013/096399
PCT Pub. Date: Jun. 27, 2013

(65) Prior Publication Data
US 2014/0324179 A1    Oct. 30, 2014

Related U.S. Application Data

(60) Provisional application No. 61/577,234, filed on Dec. 19, 2011.

(51) Int. Cl.
*A61F 2/38* (2006.01)
*A61F 2/30* (2006.01)

(52) U.S. Cl.
CPC .... *A61F 2/389* (2013.01); *A61F 2002/30136* (2013.01); *A61F 2002/30387* (2013.01);
(Continued)

(58) Field of Classification Search
CPC . A61F 2/389; A61F 2/3868; A61F 2002/3895
See application file for complete search history.

(56) References Cited

U.S. PATENT DOCUMENTS 5,282,868 A * 2/1994 Bahler ............... A61F 2/3868
623/20.29
5,336,266 A    8/1994 Caspari et al.
(Continued)

FOREIGN PATENT DOCUMENTS

CH    DE 102010008620 A1 *  8/2011  ............ A61F 2/38
CH        EP 2361592 A1 *  8/2011  ............ A61F 2/38
(Continued)

OTHER PUBLICATIONS

Translation of EP2361592 retrieved Mar. 1, 2016 from Espacenet.*
(Continued)

*Primary Examiner* — Christian Sevilla
*Assistant Examiner* — Megan Wolf
(74) *Attorney, Agent, or Firm* — Tatf Stettinius & Hollister LLP

(57) ABSTRACT

Systems, devices, and methods are described for providing orthopedic knee inserts. The orthopedic knee inserts include a surface portion having a lip configured to couple with a mating member of a tibial component, where the lip has recesses that define non-continuous contact regions between the lip and the mating member of the tibial component. Alternatively, or additionally, in certain embodiments the mating member includes a shelf for mating with an insert, the mating member having a plurality of splines disposed along the shelf that form non-continuous contact regions between the mating member and the insert.

22 Claims, 9 Drawing Sheets

(52) U.S. Cl.
CPC ............... *A61F 2002/30398* (2013.01); *A61F 2002/30401* (2013.01); *A61F 2002/30607* (2013.01)

(56) References Cited

U.S. PATENT DOCUMENTS

| | | | | |
|---|---|---|---|---|
| 5,344,460 | A * | 9/1994 | Turanyi | A61F 2/389 623/20.33 |
| 5,413,604 | A * | 5/1995 | Hodge | A61F 2/3868 623/20.28 |
| 7,740,662 | B2 * | 6/2010 | Barnett | A61F 2/3868 623/20.14 |
| 2008/0051908 | A1 | 2/2008 | Angibaud et al. | |
| 2009/0270995 | A1 | 10/2009 | Rhodes et al. | |
| 2010/0152858 | A1 * | 6/2010 | Lu | A61F 2/3886 623/20.32 |

FOREIGN PATENT DOCUMENTS

| | | |
|---|---|---|
| KR | 10-2009-0095036 | 9/2009 |
| WO | WO 2008/048819 | 4/2008 |

OTHER PUBLICATIONS

Translation of DE 102010008620 A1 retrieved from Espacenet on Sep. 13, 2016.*
International Search Report and Written Opinion, PCT Application No. PCT/US2012/070529, mailed Apr. 19, 2013 (18 pages).

* cited by examiner

ORTHOPEDIC INSERT SYSTEMS AND METHODS

CROSS-REFERENCE TO RELATED APPLICATIONS

This application is a United States National Stage filing under 35 U.S.C. §371 of International Application No. PCT/US2012/070529, filed Dec. 19, 2012, which claims the benefit of U.S. Provisional Patent Application No. 61/577,234, filed Dec. 19, 2011, each of which is hereby incorporated by reference herein in its entirety. International Application No. PCT/US2012/070529 was published under PCT Article 21(2) in English.

BACKGROUND

Total and partial knee procedures involve affixing a femoral component to the end of a patient's femur, affixing a tibial component to the end of a patient's tibia, and inserting an orthopedic insert between the tibial component and the femoral component. The insert is typically formed of a plastic material that provides a surface against which the femoral component articulates. The orthopedic insert is typically inserted into the tibial component during surgery.

The locking features of current orthopedic inserts have a continuous contact region between the mating elements of the insert and the tibial component, which can create unwanted binding between the insert and the tibial component during insertion into the tibial component. The locking features often jam due to the relatively high manufacturing tolerances required to keep the insertion forces near 10-20 pounds of force, which requires tolerances of less than about 0.003 inches. Interference along any portion of the continuous contact region can prevent the insert from being properly seated in the tibial component. Moreover, if the locking features jam due to interference, the orthopedic insert can loosen in the patient and become detached from the tibial component.

Present knee implant systems limit the techniques available to surgeons during implant procedures. For example, the orthopedic insert is typically inserted into the tibial component from an anterior-to-posterior direction. It would be desirable to allow more flexibility in the way the orthopedic insert is aligned and then placed into the tibial component.

SUMMARY

Disclosed herein are systems, devices, and methods for orthopedic inserts. In certain embodiments, the systems, devices, and methods include an orthopedic knee insert comprising a surface portion having a lip configured to couple with a mating member of a tibial component, where the lip has recesses that define non-continuous contact regions between the lip and the mating member of the tibial component. In certain embodiments, the recesses comprise cut-out portions alternately spaced between outer edges of the lip along a length of the lip. Each of the cut-out portions may have a respective recess depth. In certain embodiments, the recesses comprise portions of scalloped edges alternately spaced between outer edges of the lip along a length of the lip. Each of the recesses may have a respective recess depth. In certain embodiments, the lip of the insert is curvilinear.

In certain embodiments, the lip comprises an outer edge and an inner edge joined along a tapered edge, wherein the outer edge, inner edge, and tapered edge contact the mating member. The non-continuous contact regions defined by the recesses may be those regions where at least one of the outer edge, inner edge, and tapered edge of the lip does not contact the mating member. In certain embodiments, the lip is offset radially inwardly from a periphery of the insert. The surface area between the periphery of the insert and the offset lip may comprise a shoulder that is configured to rest on an upper surface of a tibial component. In certain embodiments, the surface portion of the insert is disposed on an inferior region of the insert. In certain embodiments, the insert further comprises a base portion from which the surface portion extends distally, wherein the base portion articulates with a femoral implant component. In certain embodiments, the lip may be disposed on the surface portion along a medial region of the insert or the lip may be disposed on the surface portion along a lateral region of the insert.

In certain embodiments, a tibial component includes a mating member with a shelf for mating with an insert, the mating member having a plurality of splines disposed along the shelf that form non-continuous contact regions between the mating member and the insert. The mating member may be disposed along a posterior region of the tibial component, or the mating member is disposed along an anterior region of the tibial component, or both. In certain embodiments, each of the splines comprises a respective spline depth. In certain embodiments, the splines may be formed from recesses made into the mating member or from projections extending from the mating member. In certain embodiments, the tibial component may be configured to receive any of the inserts discussed above.

In certain embodiments, an orthopedic implant system is provided that includes an insert, a tibial component into which the insert is positioned, and a mating surface between the insert and the tibial component defined by the surface areas along which the insert and the tibial component contact one another. The mating surface comprises non-continuous contact regions. The orthopedic implant system may further include any of the inserts and any of the tibial components discussed above.

In certain embodiments, methods for implanting an orthopedic insert in a tibial component include placing the orthopedic insert into contact with the tibial component at a first orientation, and rotating the orthopedic insert to a second orientation that locks the orthopedic insert into place in the tibial component, wherein the first orientation is offset at an angle from a posterior-to-anterior direction of tibial component. In certain embodiments, placing the orthopedic insert into the tibial component at a first orientation further comprises aligning an inferior surface of the orthopedic insert at a pitch angle with respect to a superior surface of the tibial component on which the inferior surface is placed, wherein the pitch angle is between approximately 5 to 10 degrees.

In certain embodiments, a kit for use in knee procedures is provided that includes an orthopedic insert comprising a surface portion having a lip, and a tibial component comprising a mating member with which the lip of the insert is configured to couple, wherein the lip has recesses that define non-continuous contact regions between the lip and the mating member of the tibial component.

In certain embodiments, a kit for use in knee procedures is provided that includes an orthopedic insert comprising a surface portion having a lip, and a tibial component comprising a mating member having a shelf which the lip of the insert is configured to couple, wherein the mating member comprises a plurality of splines disposed along the shelf that form non-continuous contact regions between the mating member and the insert.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, devices, and methods described herein, certain illustrative embodiments will be described. Although the embodiments and features described herein are specifically described for use in connection with orthopedic knee replacement systems, it will be understood that all the components, connection mechanisms, adjustable systems, manufacturing methods, and other features outlined below may be combined with one another in any suitable manner and may be adapted and applied to medical devices and implants to be used in other surgical procedures, including, but not limited to acetabular procedures, spine arthroplasty, cranio-maxillofacial surgical procedures, hip arthroplasty, shoulder arthroplasty, as well as foot, ankle, hand, and other extremity procedures.

Figure 1A:
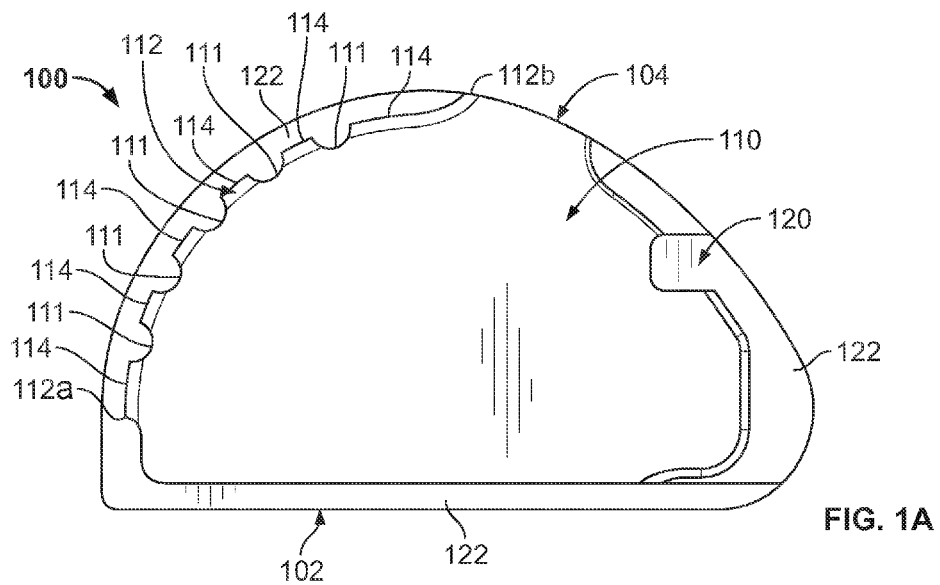
FIG. 1A shows a bottom plan view of an illustrative orthopedic insert having a lip with recesses formed into the lip.
Figure 1B:
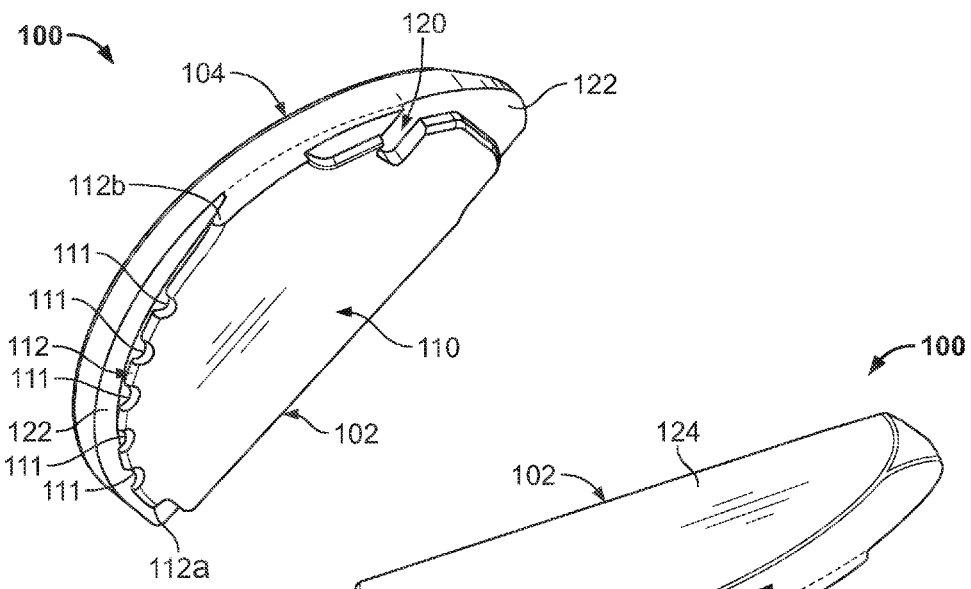
FIGS. 1B and 1C show perspective views of the illustrative orthopedic insert of FIG. 1A.
Figure 1C:
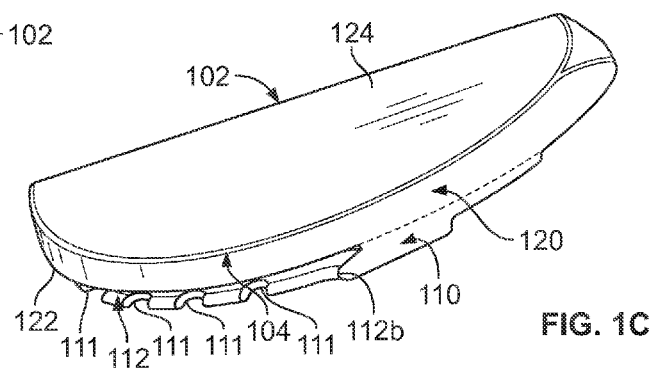

FIGS. 1A-1C show a bottom plan view and perspective views of an orthopedic insert. The orthopedic knee insert 100 shown is configured for a unicondylar implant and includes an intercondylar region 102 that is substantially linear and a medial or lateral curved region 104 that is shaped to match either the medial or lateral portion of a patient's anatomy, depending on which side of the patient the unicondylar insert will be positioned. Total and partial knee procedures involve affixing a femoral component to the end of a patient's femur, affixing a tibial component to the end of a patient's tibia, and inserting an orthopedic insert between the tibial component and the femoral component. The insert is typically formed of a plastic material that provides a surface against which the femoral component articulates. The insert 100 has an inferior surface portion 110 that extends from a superior base portion 120, the femoral surface 124 of which articulates with a femoral component. The inferior surface portion 110 typically extends distally from the patient.

The inferior surface portion 110 includes a lip 112 that extends along the periphery of the inferior surface portion 110 from a first position 112a to a second position 112b. The lip 112 is shaped to couple with a tibial component. When the insert 100 is placed into a tibial component, the lip 112 prevents the insert 100 from being dislodged or otherwise removed from the tibial component after insertion. Although the lip 112 is shown as extending from a first position 112a along the intercondylar region 102 to a second position 112b along the medial or lateral curved region 104, it will be understood that the lip 112 can have any suitable length and may be provided along any suitable region of the insert. The lip 112 may extend to a different location along the curved region 104, for example, depending on the tibial component to which the insert 100 is designed to couple. Furthermore, in certain embodiments, the insert 100 may have one or more lips that substantially surround the periphery of the inferior surface portion 110 or any other suitable portion of the insert 100.

As shown in FIGS. 1A-1C, the lip 112 has a plurality of recesses 111 formed therein. When the insert 100 is placed into a tibial component, the recesses 111 define non-continuous contact regions between the lip 112 and the tibial component. The lip 112 has five recesses 111 formed along the length of the lip 112 and alternately spaced between the outer edges 114 of the lip 112, although it will be understood that any suitable number of recesses may be formed into the lip 112. The recesses 111 that are formed into the lip 112 create alternating contact regions between the lip 112 and the mating member of a tibial component into which the insert is placed, such as mating member 160 of the tibial component 150 of FIG. 2.

The recesses 111 of FIGS. 1A-1C are formed as cutouts made from the lip 112. Each of the recesses 111 has a respective recess depth, and although the depth of each recess 111 is shown as being substantially the same, it will be understood that any suitable depth may be used and each respective recess need not have the same depth as the other recesses.

In addition to reducing the contact between the lip 112 and a tibial component, the cutouts allow the material of the insert 100, for example polyethylene or any other suitable material, to deform into the lock detail of the tibial component. This helps compensate for any manufacturing dimensions that require high tolerance. In other words, because the lip 112 has recessed portions 111, shown in FIGS. 1A-1C as cutouts, the lip 112 is able to deform in relatively more degrees of freedom when coupled to a tibial component than it would otherwise be able to deform if the lip did not have recessed portions. This allows greater variability of manufacturing tolerances because the lip 112 can deform into areas within the recess or channel of the tibial component without having to deform against the typically metal material of the tibial component. The recesses 111 formed in the lip 112 are shown as half circles, although it will be understood that any other suitable shape or combinations thereof may be cutout from the lip 112. The recesses 111 reduce the relative contact surface area between the lip 112 and the mating member of the tibial component as will be explained in more detail below.

Figure 2:
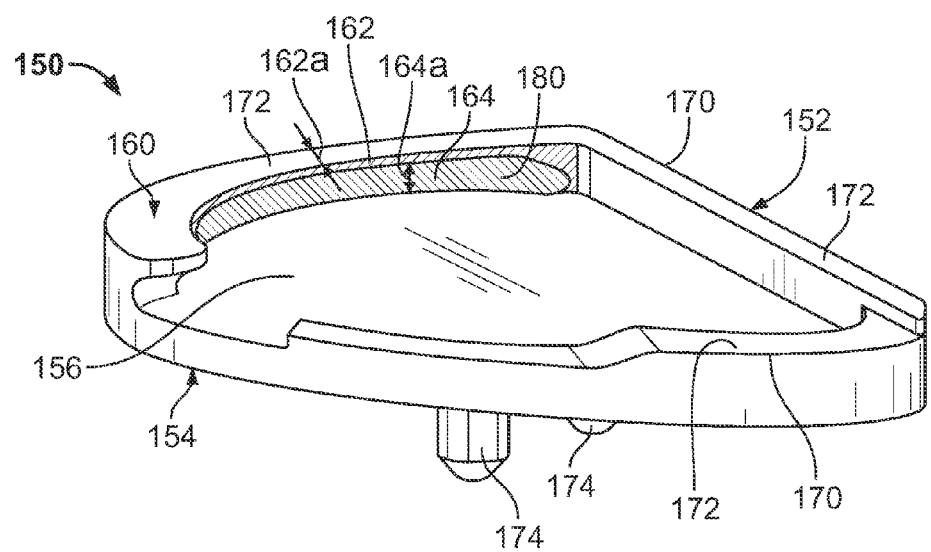
FIG. 2 shows a perspective view of an illustrative tibial component.

As shown in FIG. 1B, the inferior surface portion 110 extends from a superior base portion 120 and is configured to interface with a surface of a tibial component, such as the inset superior surface 156 of the tibial component 150 of FIG. 2. A shoulder 122 extends along the periphery of the insert 100 and surrounds the inferior surface portion 110. The shoulder 122 rests on complementary surfaces of a tibial component when the insert 100 is placed within the tibial component, such as the upper surface 172 of the tibial component 150 of FIG. 2. FIG. 1C shows that the base portion 120 includes a femoral surface 124 on the superior side of the insert 100, where the femoral surface 124 is configured to articulate with a femoral implant component that is typically a part of a knee implant system, which includes a femoral component, an insert, and a tibial component.

FIG. 2 shows a perspective view of a tibial component that is configured to receive an insert, such as insert 100 of FIGS. 1A-1C. As shown in FIG. 2, the tibial component 150 includes an intercondylar region 152 and a medial or lateral curved region 154 that is shaped to match either the medial or lateral portion of a patient's anatomy. These regions 152 and 154 are shaped to mate with corresponding regions on the insert, such as intercondylar region 102 and medial or lateral curved region 104 of the insert 100 of FIGS. 1A-1C. The respective intercondylar regions align the insert 100 with the tibial component 150 to assist with placing the insert into the tibial component 150 by providing a point of reference to the surgeon, that is, the similarly shaped curved regions.

Figure 3:
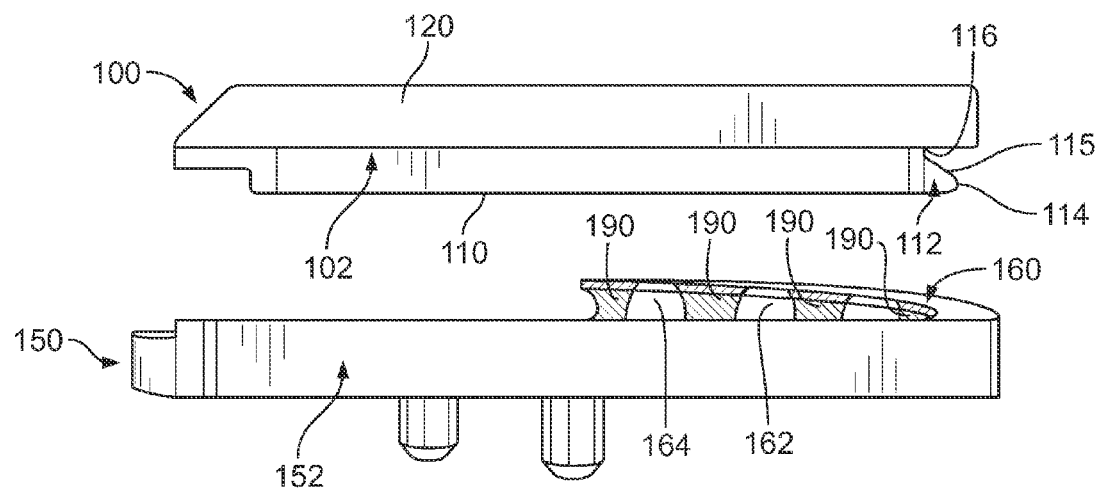
FIG. 3 shows an exploded perspective view of the orthopedic insert of FIGS. 1A-1C and the tibial component of FIG. 2.

The tibial component 150 also includes an inset superior surface 156 that provides a seat upon which the inferior surface portion of an insert is placed, such as the inferior surface portion 110 of the insert 100. In order to prevent an insert from becoming dislodged or otherwise moving after placement within the tibial component, the tibial component 150 includes a mating member 160 having a shelf 162 and an arced channel 164 that is positioned between the mating member 160 and the inset superior surface 156. The mating member 160 extends from the intercondylar region 152 to a position along the medial or lateral curved region 154. The shelf 162 of the mating member 160 extends inwardly from a periphery of the tibial component 150 and has a depth 162a from the edge of the tibial component 150 that substantially matches the depth of an insert shoulder, such as the shoulder 122 of insert 100. The channel 164 can have any suitable height 164a within which the lip of an orthopedic insert is placed. The dimensions of the mating member 160 substantially correspond to those of a coupling component of the insert, such as the lip 112 of insert 100. For example, the mating member 160, having a shelf 162 with an arced channel 164, matches and abuts the lip 112 of the insert 100 thereby forming an interface to secure the two components. Illustrative interfaces 180 and 190 are shown in FIGS. 2 and 3. For example, a continuous interface region 180 is shown along the mating member 160 of FIG. 2. When an insert having a lip without recesses is placed into the mating member 160, the contact region between the lip and the mating member is continuous along the interface region 180. However, as discussed above, such a continuous contact region between the insert and the mating member may not be desirable because the insertion forces required to place such an insert may be substantial. A non-continuous contact region 190 is shown in FIG. 3. When an insert having recessed portions, such as insert 100, is placed into the mating member 160, the contact region between the lip 112 and the mating member 160 is non-continuous as shown by non-continuous interface region 190.

The tibial component 150 includes a ledge 170 that extends from the inset superior surface 156 and along the length of the intercondylar region 152 and a portion of the medial or lateral curved region 154. An upper surface 172 of the ledge 170 extends along the entirety of the ledge 170 and extends continuously to the upper surface of the mating member 160. The upper surface 172 is configured to mate with the shoulder 122 of the insert 100. The shape and other dimensions of the insert shoulder substantially conform to the shape of the upper surface 172 upon which the shoulder is seated.

The tibial component 150 includes one or more boss members or pegs 174 that extend within a patient's anatomy and, in particular, within a proximal resected surface of the patient's tibia. The boss members or pegs 174 are shown as being substantially cylindrical, although it will be understood that they can have any suitable shape and depth.

FIG. 3 shows an exploded perspective view of the orthopedic insert 100 and tibial component 150. The lip 112 of the orthopedic insert 100 includes an outer edge 114 and an inner edge 116 joined along a tapered edge 115. The insert 100 is configured to be placed within the mating member 160 of the tibial component 150. The lip 112 mates with the mating member 160 by extending into the channel 164 along the shelf 162 of the mating member 160. In particular, the outer edge 114 and the tapered edge 115 of the lip 112 extend into the channel 164 and make contact, for example, between the shelf 162 and the tapered edge 115, thereby preventing the insert 100 from becoming dislodged or otherwise removed from the tibial component 150. As shown on FIG. 3, the intercondylar regions 102, 152 of the insert 100 and tibial component 150, respectively, are aligned (and therefore so are the medial or lateral regions) in order to place the insert 100 into the tibial component 150.

Figure 4:
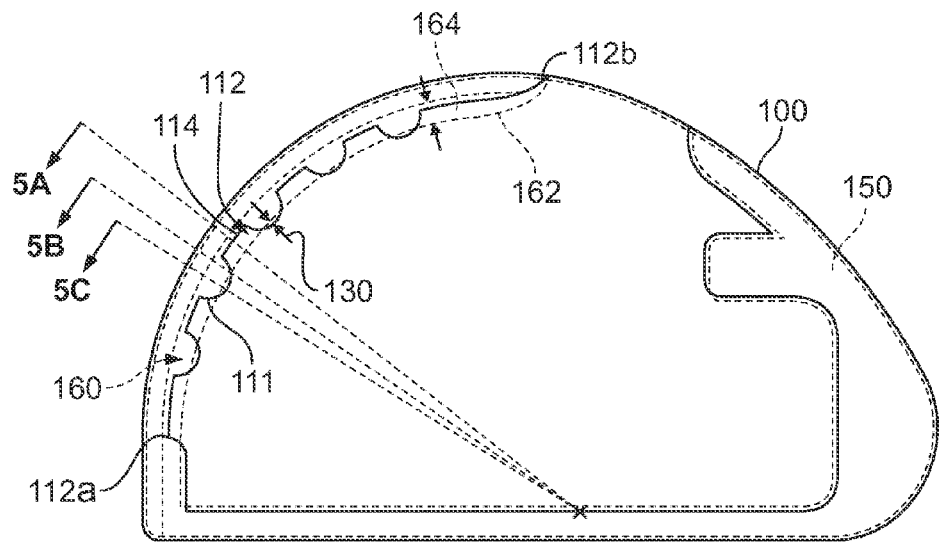
FIG. 4 shows a bottom plan view of the illustrative orthopedic insert of FIGS. 1A-1C coupled with the tibial component of FIG. 2.

FIG. 4 shows a bottom plan view of the orthopedic insert 100 of FIGS. 1A-1C coupled with the tibial component 150 of FIG. 2, the tibial component shown using dotted lines. The lip 112 extends from the first position 112a to the second position 112b. Overlaid over the lip 112 is a mating member 160 having a shelf 162 and a channel 164. As shown, various contact regions are situated between the lip 112 of the insert 100 and the mating member 160 of the tibial component 150.

Figure 5A:
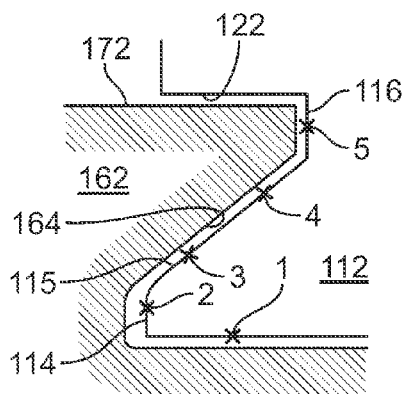
FIGS. 5A-5C show illustrative partial cross-sectional views of the interface between the orthopedic insert and tibial component of FIG. 4.
Figure 5B:
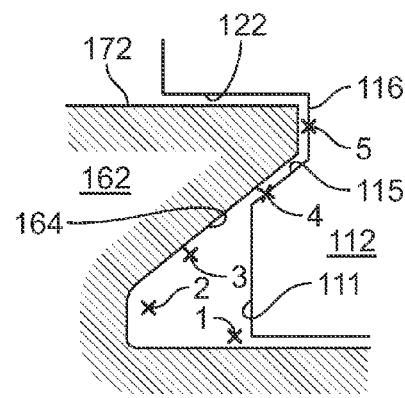
Figure 5C:
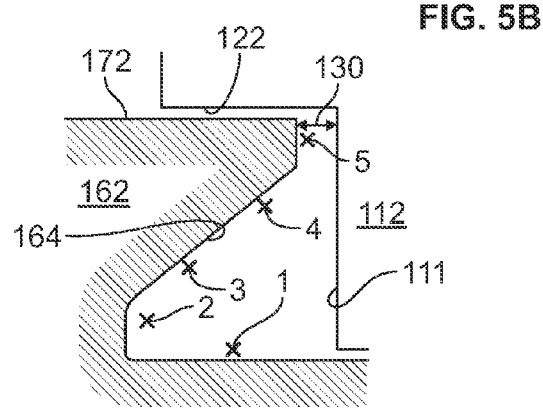

FIGS. 5A-5C show partial cross-sectional views of the interfaces formed by the contact regions of the insert 100 and the tibial component 150 of FIG. 4. Each of the cross-sectional views includes five contact regions labeled regions 1 through 5, along which the lip 112 and the mating member 160 may contact one another. FIG. 5A shows the interface taken along line 5A of FIG. 4, where the lip 112 includes an outer edge 114 and an inner edge 116 joined along a tapered edge 115. The lip 112 couples with the mating member 160 by extending into the channel 164 along the shelf 162. In particular, the outer edge 114 and the tapered edge 115 of the lip 112 extend into the channel 164 and make contact between the lip 112 and the mating member 160, thereby preventing the insert 100 from becoming dislodged or otherwise removed from the tibial component 150. Shown along the interface of the lip 112 and the mating member 160 are the five contact regions labeled regions 1 through 5 along which the lip 112 and the mating member 160 may contact one another. Region 1 extends along the distal surface the lip 112. Region 2 extends along the outer edge 114 of the lip 112. Regions 3 and 4 extend along the tapered edge 115 of the lip 112, and region 5 extends along the inner edge 116 of the lip 112. As shown in FIG. 5A, for example, contact is made between the insert 100 and the tibial component 150 along each of the five contact regions. Furthermore, as shown in FIG. 5A, the shoulder 122 of the insert 100 is seated along the upper surface 172 of the mating member 150. In certain embodiments, the outer edge 114 of the lip 112 may not contact the mating member 160 along region 2, yet the insert 100 may still be securely positioned within the tibial component 150.

FIG. 5B shows a partial cross-sectional view of the interface taken along line 5B of FIG. 4, which is halfway between the outer most edge 114 of the lip 112 and the inner most part of the recess 111. As shown in FIG. 5B, the lip 112 has been cutout to the recessed portion 111, thereby removing material that was present in FIG. 5A. In particular, the outer edge 114 of the lip 112 present in FIG. 5A has been removed and the tapered edge 115 has been shortened relative to that shown in FIG. 5A. The inner edge 116 of the lip 112 in FIG. 5B is substantially the same as that shown in FIG. 5A. Of the five contact regions 1-5, the lip 112 now only contacts regions 4 and 5. The contact with regions 4 and 5 is continuous between the portions of the lip 112 shown in FIGS. 5A and 5B. The contact between the lip and the mating member along regions 1, 2, and 3, however, is not continuous and therefore these regions are non-continuous contact regions between the lip 112 and the tibial component 150.

FIG. 5C shows a partial cross-sectional view of the interface taken along line 5C of FIG. 4, which is the fully recessed portion of the lip 112. As shown in FIG. 5C, the lip 112 has been fully recessed such that there is no contact along any of regions 1-5. Therefore, any of regions 1-5 comprises non-continuous contact regions between the lip 112 and the tibial component 150. Furthermore, there is a distance 130 between the shelf 162 and the lip 112 that was not present in the cross-sections of FIGS. 5A and 5B. As shown in each of FIGS. 5A-5C, the shoulder 122 of the insert 100 rests against the upper surface 172 of the mating member 150.

Figure 6:
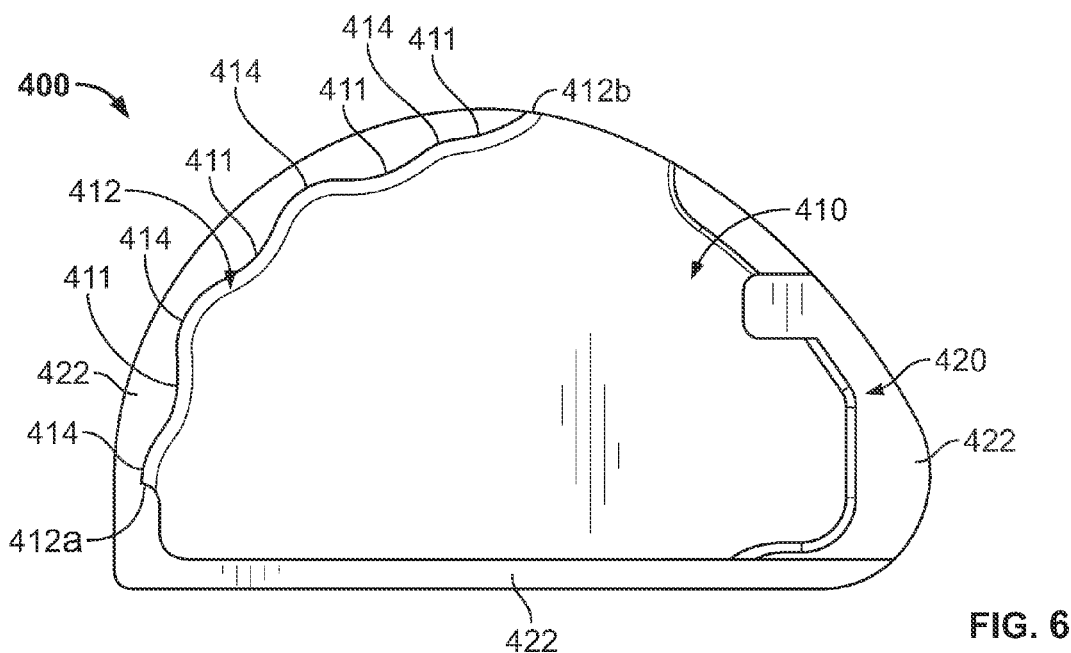
FIG. 6 shows a bottom plan view of an illustrative orthopedic insert having a lip with recesses formed into the lip.

Various types of recesses can be formed into the lip of an orthopedic insert. FIG. 6 shows a bottom plan view of an orthopedic insert 400 having a curvilinear lip 412 with recesses 411 formed therein. When the insert 400 is placed into a tibial component, such as tibial component 150 of FIG. 2, the recesses 411 define non-continuous contact regions between the lip and the tibial component. Unlike the recesses 111 of FIGS. 1A-1C which are formed as cutouts, the recesses 411 of FIG. 6 are portions of scalloped edges alternately spaced between outer edges 414 of the lip 412 along the length of the lip 412 from the first position 412a to the second position 412b. Compared to the recesses 111 of FIGS. 1A-1C, the recesses 411 are continuous and smooth along the length of the lip 412, whereas the recesses 111 of FIGS. 1A-1C are continuous but not smooth. The recesses 411 of FIG. 6 alternate along the length of the lip 412 such that the lip 412 has certain outer portions 414 along the edge of the lip 412 and inner portions on the inner part of the recess 411. Each of the recesses 411 has a respective recess depth, and although the depth of each recess 411 is shown as being substantially the same, it will be understood that any suitable depth may be used and each respective recess need not have the same depth as the other recesses. The recesses 411 that are formed into the lip 412 create alternating contact regions between the lip 412 and the mating member of a tibial component into which the insert is placed, such as mating member 160 of the tibial component 150 of FIG. 2. The orthopedic knee insert 400 also includes a superior base portion 420 from which the inferior surface portion 410 extends, as well as a shoulder 422 that substantially encircles the inferior surface portion 410. The shoulder 422 rests on complementary surfaces of a tibial component when the insert 400 is placed within the tibial component, such as the upper surface 172 of the tibial component 150 of FIG. 2.

Figure 7:
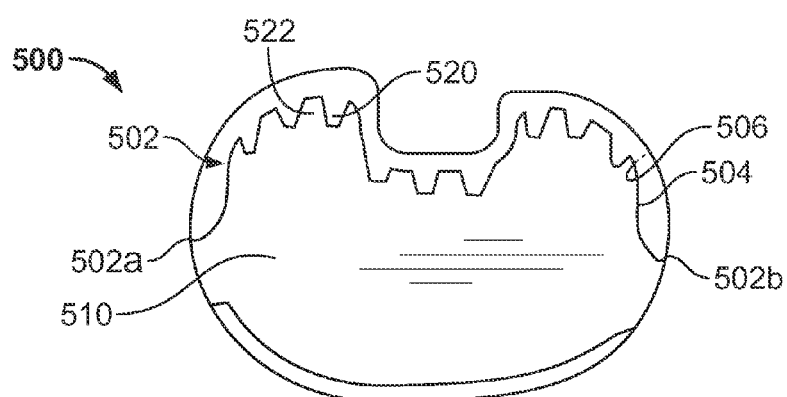
FIGS. 7-9 show a top plan views of illustrative tibial components having splines.
Figure 8:
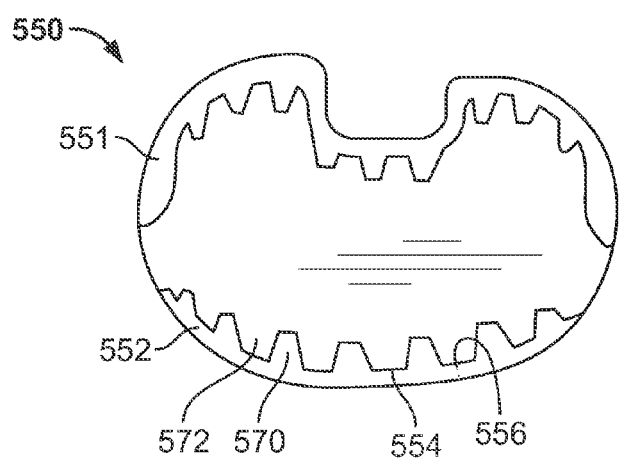
Figure 9:
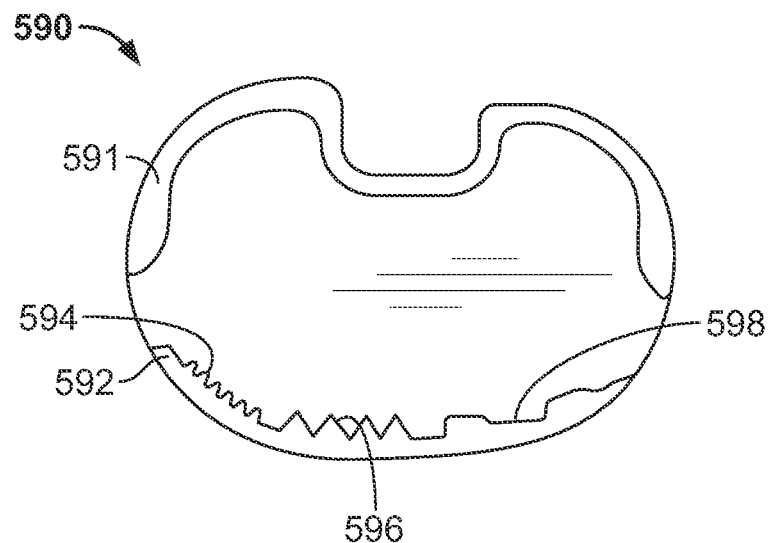

FIGS. 7-9 show various top plan views of tibial components having recessed portions that form splines for reducing the contact area between an insert and the tibial component and preventing the insert placed therein from being dislodged or otherwise removed from the tibial component after insertion. The recessed portions and splines create non-continuous contact regions between the tibial component and the insert, whether the insert has a lip with recesses or not. As shown in FIG. 7, for example, a tibial component 500 includes a mating member 502 extending from a first position 502a to a second position 502b along the posterior portion of the component 500. Although the mating member 502 of tibial component 500 has a length from first position 502a to second position 502b, it will be understood that mating member 502 can have any suitable length. The mating member 502 has a shelf 504 and an arced channel 506 that is positioned between the mating member 160 and the inset superior surface 510 and extends along the length of the mating member 502. Similar to the tibial component shown in FIG. 2, the tibial component 500 includes an inset superior surface 510 upon which an insert may be placed. The mating member 502 includes a plurality of recessed portions 522 that form splines 520 along the length of the mating member 502. The splines 520 form a wedge fit that stabilizes an insert in substantially all directions, including rotational stability, thereby preventing micro-motion and backside wear. Furthermore, the splines 520, disposed along the shelf 504 of the mating member 502, form non-continuous contact regions between the mating member 502 and an insert. As shown in FIG. 7, each of the splines 520 has a respective spline depth depending on the extent to which the recessed portions 522 extend into the mating member 502. Any suitable depth may be used and each respective spline need not have the same depth as the other splines, although in certain embodiments each of the splines 520 may have the same spline depth. The tibial component 500 can be used with inserts having lips with or without recessed portions. In certain embodiments, splines may be provided by forming projections extending from the mating member, rather than, or in addition to, forming the splines from recessing portions in the mating member. While FIG. 6 shows a mating member 502 that is continuous across its length, in certain embodiments, the mating member 502 may include gaps, for example, and not be continuous.

In certain embodiments, the tibial component includes a mating member along the anterior portion of the tibial component. Additional splines located on the anterior portion of the tibial component may be used to further lessen the force requirement to lock the orthopedic insert into the tibial component. For example, as shown in FIG. 8, tibial component 550 includes an anterior mating member 552 having a shelf 554, a channel 556 therein, and a plurality of recessed portions 572 and splines 570. Each of the splines 570 has a respective spline depth depending on the extent to which the recessed portions 572 extend into the anterior mating member 552. Any suitable spline depth may be used and each respective spline need not have the same depth as the other splines, although in certain embodiments each of the splines 570 may have the same spline depth. Anterior mating member 552 may have any suitable length. The tibial component 550 also includes a posterior mating member 551 that is substantially similar to that shown in FIG. 7. While FIG. 8 shows an anterior mating member 552 and a posterior mating member 551 that are continuous across their respective lengths, in certain embodiments, the anterior mating member 552 and/or the posterior mating member 551 may include gaps, for example, and not be continuous. In certain embodiments, anterior mating member 552 may be extended such that the anterior mating member 552 and posterior mating member 551 are joined.

In certain embodiments, there may be provided any suitable spline pattern or combination of spline patterns formed by recesses in the mating member. For example, as shown in FIG. 9, the tibial component 590 includes an anterior mating member 592 having a first spline pattern 594, a second spline pattern 596, and a third spline pattern 598. It will be understood that any combination of these spline patterns 594, 596, 598, or any other suitable spline patterns, may be provided. Furthermore, in certain embodiments, splines may be provided on the posterior mating member 591 or the anterior mating member 592 or both. For example, although not shown in FIG. 9, the posterior mating member 591 may also include splines.

In certain embodiments, any one or more of the orthopedic inserts described herein (e.g., orthopedic inserts 100, 400) may be provided in a kit. The kit may further include a tibial component (e.g., tibial component 150) that is configured to receive any of the orthopedic inserts provided in the kit. In certain embodiments, the tibial component includes a mating member having a shelf with a plurality of splines.

Figure 10:
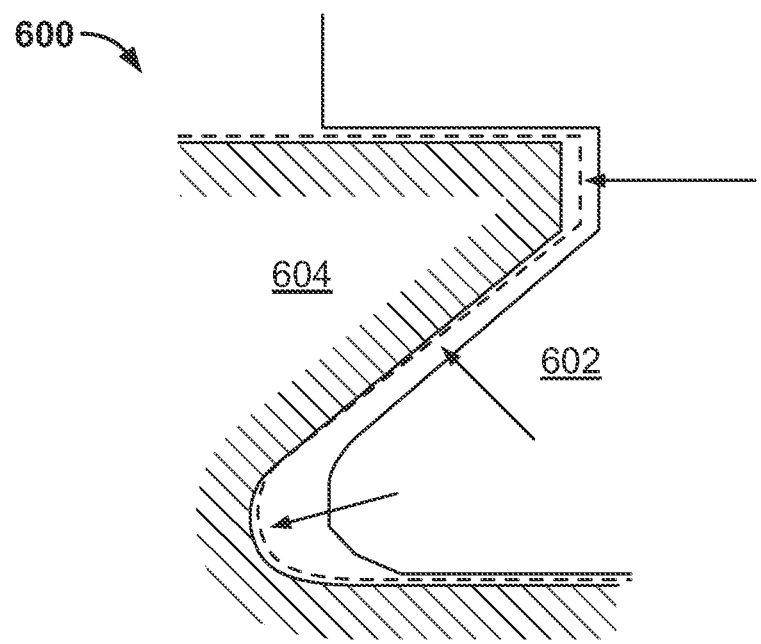
FIG. 10 shows a partial cross-sectional view of an illustrative interface between an orthopedic insert and a tibial component.

By creating non-continuous contact regions, for example, using an insert with recessed portions or a tibial component with splines, or both, the force required to place an insert into a tibial component can be reduced. Another way to reduce insertion forces alternatively or additionally relies on the properties of the materials used for the insert and/or tibial component. FIG. 10 shows a partial cross-sectional view of an interface between a tibial component and an orthopedic insert having thermal expansion properties. As shown in FIG. 10 the orthopedic insert 602 joins the tibial component 604 across the interface 600. The orthopedic insert 602 is shown at two different states. The first is a profile of the orthopedic insert at operating room temperature (shown by the solid line). The second is a profile of the orthopedic insert at body temperature (shown by the dotted line). The operating room temperature is normally around 65 degrees Fahrenheit and body temperature is normally around 98 degrees Fahrenheit. Given the thermal coefficient of expansion for the material, such as polyethylene, the design lock feature between the insert and the tibial component (e.g., a "tongue and groove" or "dovetail" lock) may be designed such that when the insert expands in the body it fills substantially all voids, gaps, and/or head space within the channel of the tibial component. The design can be optimized by using software. The expansion of the orthopedic insert may allow designs having relatively less tolerance than current designs, because the expansion of the orthopedic insert makes up for any differences in design arising during manufacture.

Figure 11:
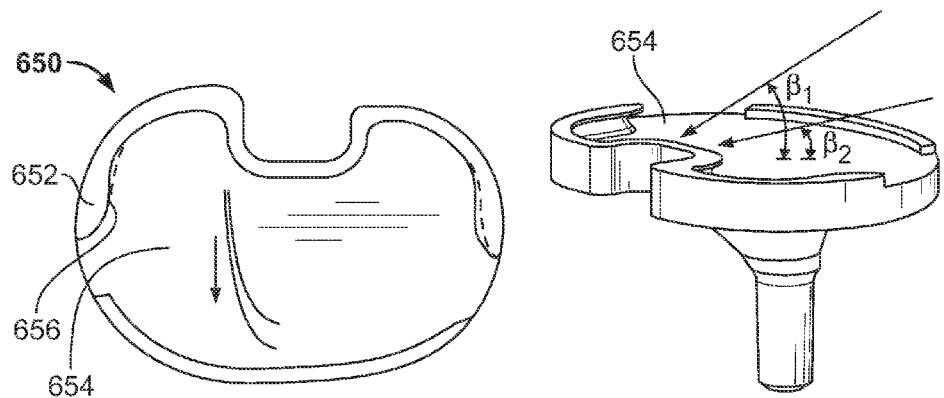
FIG. 11 shows a top plan view and a perspective view, respectively, of an illustrative tibial component having optimized curved mating surfaces.

The insert and the tibial component can be structured so as to make it relatively easier to place the insert into the tibial component within a surgical window. FIG. 11 shows a top plan view and a perspective view, respectively, of a tibial component having optimized curved mating surfaces to allow for a relatively lower angle of insertion for placing the insert into the tibial component. The tibial component 650 includes a mating member 652 having flat portions 656. The flat portions 656 may optionally be eliminated so that an insert can be placed into the tibial component 650 at a relatively lower pitch angle of insertion. Such angles of insertion include about 20 degrees or less, about 10 degrees or less, or about 5-10 degrees. The orthopedic insert is typically inserted from the anterior-to-posterior direction at a pitch angle $\beta_1$ with respect to an inferior surface of the orthopedic insert (e.g., inferior surface portion 110 of FIG. 1A) and a superior surface 654 of the tibial component 650 on which the orthopedic insert is positioned. A relatively lower angle of insert, pitch angle $\beta_2$ as compared to pitch angle $\beta_1$, allows a surgeon to operate in a relatively more confined operating window within the patient. By eliminating the flat portion 656 of the tibial component 650, the insert can be placed at the relatively lower angle for insertion.

Figure 12:
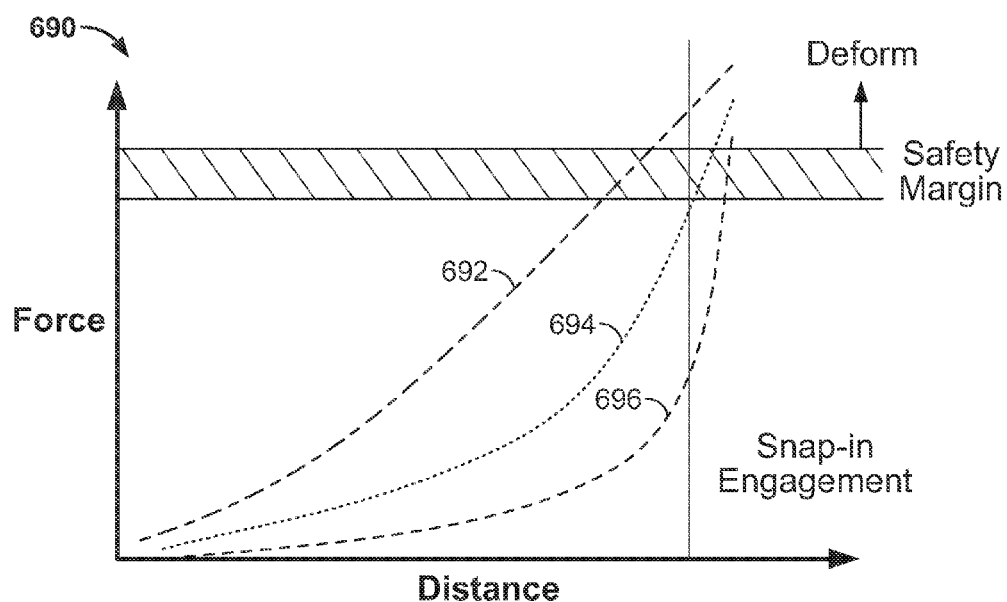
FIG. 12 is a graphic comparing force against distance for optimizing the curved mating surfaces of the tibial component of FIG. 11.

The insert design balances the deformation and strength of the insert with ease of insertion and resistance to removal. FIG. 12 is a graphic that plots force against distance for optimizing the curved mating surfaces of the tibial component 650 of FIG. 11. Along one axis is force and along a second axis is distance. Shown at an extreme of the force axis is a safety margin above which the plastic insert will deform. Shown along the distance axis is the distance at which snap-in engagement occurs. Line 692 shows a profile where the force required for inserting an insert exceeds the safety margin prior to snap-in engagement. Line 694 shows a profile where snap-in engagement occurs just prior to the safety margin of force. However, the force necessary to snap-in the insert may be higher than is possible or even practical to achieve during surgery. Line 696 shows a profile where snap-in engagement occurs at a force that is substantially less than the force required by the profiles of lines 692 and 694 for inserting the insert within a safety margin. Preferably, an orthopedic insert snaps into a tibial component with a force that is less than the safety margin force and within practical values achievable during surgery.

Figure 13:
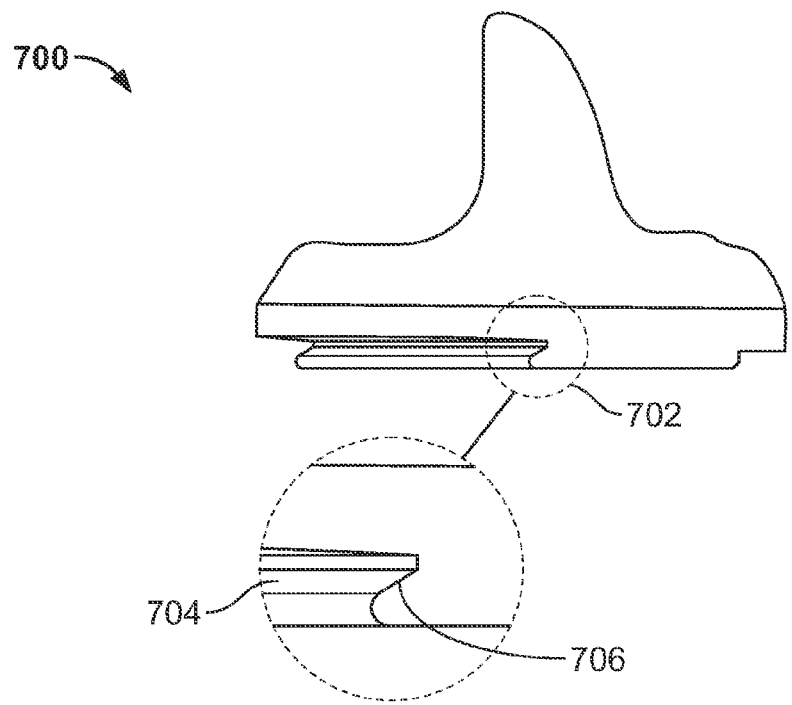
FIG. 13 shows a side elevation view of an illustrative orthopedic insert having an interface region.
Figure 14:
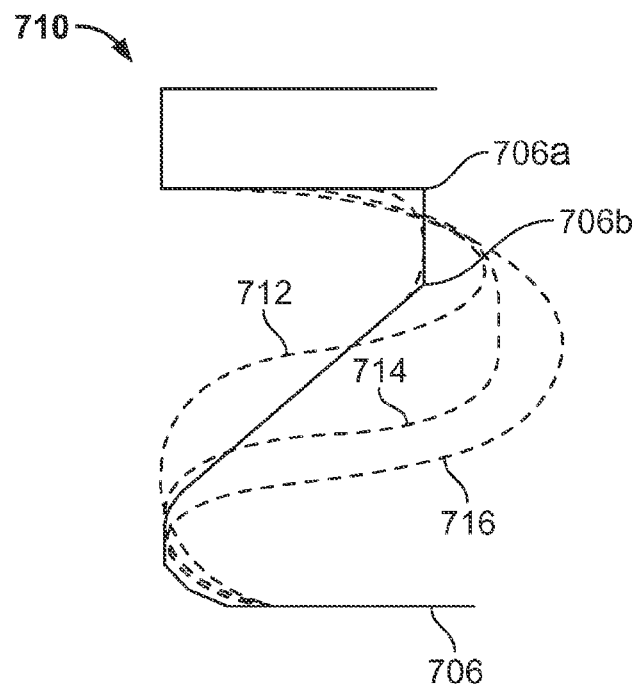
FIG. 14 shows a schematic cross-sectional of illustrative profiles for the interface region of FIG. 13.

In certain embodiments, the profile of the interface region on the insert may be modified to improve the deformation and strength of the insert while still balancing ease of insertion and resistance to removal. FIG. 13 shows a side elevation view of an orthopedic insert having an interface region. Orthopedic insert 700 has an interface region 702 that includes a lip 704 and a contact profile 706. The contact profile 706 as shown in FIG. 14 includes regions 706a, 706b of increased stress concentrations at the corners of the contact profile 706. Alternate contact profiles 712, 714, and 716 decrease stress concentrations by using fillets and curved profiles, thus altering the contact profile 706 of the interface region 702. While FIG. 14 shows examples of contact profile shapes, it will be understood that any suitable alternate contact profile shape may be used. For example, alternate contact profiles may include dovetail shapes that can reduce deformation, promote elastic, and not plastic, deformation, and decrease chances of accidental cracking Accidental cracking can occur in orthopedic inserts or tibial components at locations of high stress concentrations. Alternate contact profiles 712, 714, and 716 decrease stress concentrations and thus decrease the risk of accidental cracking during insertion. Furthermore the alternate contact profiles provide a decreased chance of insertion error or misalignment during the surgical procedure.

Figure 15:
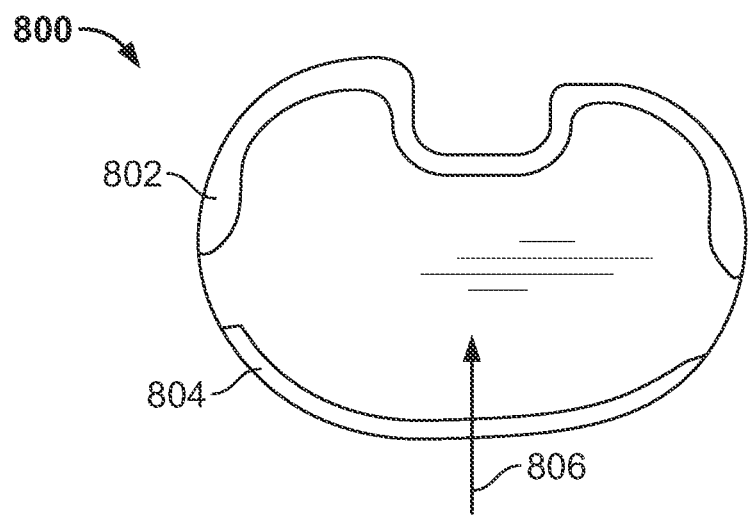
FIGS. 15-17 show various top plan views of illustrative tibial components for radially-offset insertion of an orthopedic insert.
Figure 16:
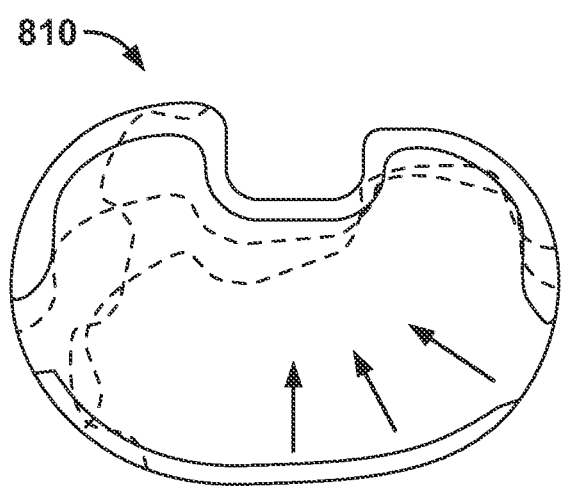
Figure 17:
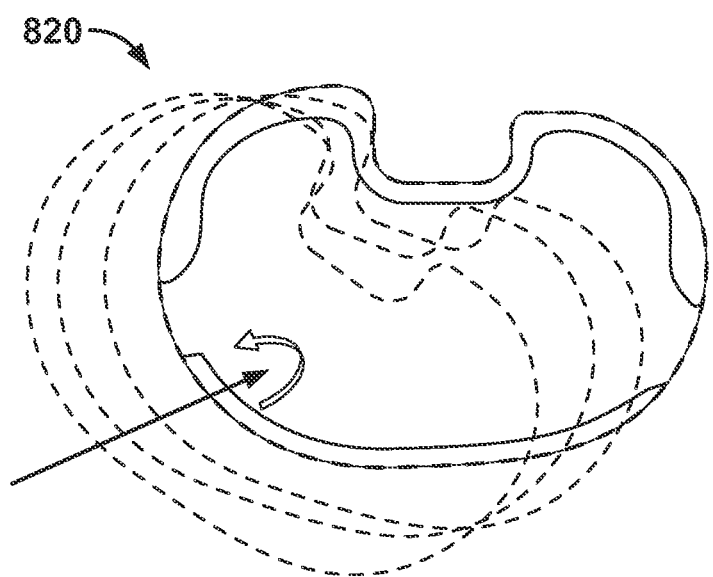

As discussed above, the insert and the tibial component can be structured so as to make it relatively easier to place the insert into the tibial component within a surgical window. Alternatively, or additionally, the insert and tibial component can be structured to provide for radially offset insertion. FIGS. 15-17 show various top plan views of tibial components for radially offset insertion of an orthopedic insert. Currently, orthopedic inserts are inserted in an anterior-to-posterior direction as shown by arrow 806 of FIG. 15. However, in some embodiments, a surgeon may wish to adjust the insertion angle for the approach during surgery. FIG. 16 shows various angles at which an insert may be positioned into a tibial component 810. In some embodiments, orthopedic insert 820 may be provided that may be translated and then rotated to lock the insert into place in the tibial component. For example, an orthopedic insert may be placed into contact with a tibial component at a first orientation that is offset at an angle with respect to the anterior-to-posterior direction as shown by arrow 806. The orthopedic insert may then be rotated into a second orientation that aligns with the tibial component and locks the orthopedic insert into place in the tibial component. By providing offset angles for placement of the insert into the tibial component, the surgeon has more options during surgery regarding the size and type of incisions that need to be made in a patient.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in knee systems, may be applied to systems, devices, and methods to be used in other surgical procedures including, but not limited to, spine arthroplasty, cranio-maxillofacial surgical procedures, hip arthroplasty, shoulder arthroplasty, as well as foot, ankle, hand, and extremities procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. An orthopedic knee implant system, comprising:
   an orthopedic insert having a surface portion having a lip configured to couple with a mating member of a tibial component, the orthopedic insert including a shoulder positioned along a periphery of the orthopedic insert, the lip positioned at an inwardly recessed location beneath the shoulder; and
   a tibial component having at least one mating member having a shelf and a recess, the shelf inwardly extending continuously over the recess, the shelf having an upper surface and a plurality of recesses, the upper surface structured to abut the shoulder, the plurality of recesses being recessed into the shelf along a length of an interior portion of the shelf, the plurality of recesses defining regions of non-continuous contact between the orthopedic insert and the interior portion of the shelf.

2. The orthopedic knee implant system of claim 1, wherein the plurality of recesses comprise cut out portions alternately spaced along the shelf.

3. The orthopedic knee implant system of claim 2, wherein each of the cut-out portions comprises a respective recess depth, and wherein the respective recess depth of one or more of the plurality of recesses is different than a respective recess depth of another of the plurality of recesses.

4. The orthopedic knee implant system of claim 3, wherein the plurality of recesses comprise portions of scalloped edges alternately spaced along the shelf.

5. The orthopedic knee implant system of claim 1, wherein each of the plurality of recesses comprises a respective recess depth, and wherein the respective recess depth of one or more of the plurality of recesses is different than a respective recess depth of another one of the plurality of recesses.

6. The orthopedic knee implant system of claim 1, wherein the lip is curvilinear.

7. The orthopedic knee implant system of claim 1, wherein the lip comprises an inner edge and an outer edge, the outer edge having an upper edge, a lower edge, and a tapered edge, the tapered edge outwardly extending from the upper edge to the lower edge, wherein at least a portion of the outer edge and the inner edge define continuous contact regions of the lip.

8. The orthopedic knee implant system of claim 7, wherein the regions of non-continuous contact defined by the plurality of recesses include regions where at least a portion of at least one of the upper edge, lower edge, and tapered edge of the lip does not contact the mating member.

9. The orthopedic knee implant system of claim 7, wherein the tapered edge is outwardly tapered away from the upper edge to the lower edge such that the inner edge is inwardly recessed beneath the shoulder by a first recessed distance that is greater than a second recessed distance that the lower edge is recessed beneath the shoulder.

10. The orthopedic knee implant system of claim 9, wherein the lip is offset radially inwardly from a periphery of the insert, and wherein a surface area between the periphery of the insert and the lip comprises the portion of the shoulder that is configured to abut the upper surface of the tibial component.

11. The orthopedic knee implant system of claim 1, wherein the surface portion is disposed on an inferior region of the insert.

12. The orthopedic knee implant system of claim 1, wherein the insert further comprises a base portion from which the surface portion extends distally, wherein the base portion articulates with a femoral implant component.

13. The orthopedic knee implant system of claim 1, wherein the lip is disposed on the surface portion along a medial region of the insert.

14. The orthopedic knee implant system of claim 1, wherein the lip is disposed on the surface portion along a lateral region of the insert.

15. A tibial component comprising:
an inset superior surface, at least one mating member, and an arced channel, the at least one mating member having a shelf for mating with an insert, the arced channel positioned between the shelf and the inset superior surface, the shelf inwardly extending continuously over the arced channel, the shelf of the at least one mating member having a plurality of splines and a plurality of recesses recessed into the shelf, the plurality of recesses defining regions of non-continuous contact between the shelf and the insert, the plurality of splines sized to facilitate a wedge fit between the insert and the tibial component.

16. The tibial component of claim 15, wherein the at least one mating member is disposed along a posterior region of the tibial component.

17. The tibial component of claim 15, wherein the at least one mating member is disposed along an anterior region of the tibial component.

18. The tibial component of claim 15, wherein each of the plurality of splines comprises a respective spline depth.

19. The tibial component of claim 18, wherein the respective spline depth of one or more of the plurality of splines is different than the respective spline depth of another of the plurality of splines.

20. An orthopedic implant system, comprising:
an insert having a lip and a shoulder, the lip including an outer edge positioned at an inwardly recessed location beneath the shoulder;
a tibial component into which the insert is positioned, the tibial component having an inset superior surface, a mating member and an arced channel, the arced channel positioned between the mating member and the inset superior surface, the mating member having a shelf that inwardly extends continuously over the arced channel, the arced channel sized to receive insertion of at least a portion of the outer edge, the shoulder structured to abut an upper surface of the mating member; and
a plurality of recesses being recessed into both the outer edge and the shelf, the plurality of recesses structured to define regions of non-continuous contact between the outer edge and the shelf.

21. A kit for use in knee procedures, the kit comprising:
an orthopedic insert comprising a surface portion having a lip, the lip positioned at an inwardly recessed location beneath a shoulder of the orthopedic insert; and
a tibial component comprising a mating member with which the lip of the insert is configured to couple;
wherein the mating member has at least one shelf that inwardly extends continuously over an arced channel in the tibial component, the at least one shelf having a plurality of recesses, an outer edge of the lip arranged to contact an interior portion of the arced channel, the plurality of recesses being recessed into the at least one shelf to define regions of non-continuous contact in-between areas of continuous contact between the orthopedic insert and the at least one shelf of the tibial component.

22. A kit for use in knee procedures, the kit comprising:
an orthopedic insert comprising a surface portion having a lip; and
a tibial component comprising at least one mating member, an inset superior surface, and an arced channel, the mating member having a shelf which a portion of the lip of the insert is configured to couple, the arced channel positioned between the shelf and the inset superior surface, the shelf extending continuously over the arced channel;
wherein the shelf includes a plurality of splines and a plurality of recesses, the plurality of recesses being disposed along the shelf and form non-continuous contact regions between the shelf and the orthopedic insert.

* * * * *